(12) United States Patent
Helton et al.

(10) Patent No.: US 9,918,949 B2
(45) Date of Patent: Mar. 20, 2018

(54) EMESIS TREATMENT

(71) Applicant: REPURPOSED THERAPEUTICS, INC., Tampa, FL (US)

(72) Inventors: David Helton, Dana Point, CA (US); James Lucot, Dayton, OH (US)

(73) Assignee: Repurposed Therapeutics, Inc., Tampa, FL (US)

( * ) Notice: Subject to any disclaimer, the term of this patent is extended or adjusted under 35 U.S.C. 154(b) by 0 days.

(21) Appl. No.: 14/447,518

(22) Filed: Jul. 30, 2014

(65) Prior Publication Data

US 2015/0005388 A1      Jan. 1, 2015

Related U.S. Application Data

(63) Continuation of application No. 13/501,531, filed as application No. PCT/US2010/052961 on Oct. 15, 2010, now abandoned.

(60) Provisional application No. 61/252,291, filed on Oct. 16, 2009.

(51) Int. Cl.
  *A61K 31/135*      (2006.01)
  *A61K 31/13*       (2006.01)

(52) U.S. Cl.
  CPC ............ *A61K 31/135* (2013.01); *A61K 31/13* (2013.01)

(58) Field of Classification Search
  USPC .......................................... 514/657; 564/428
  See application file for complete search history.

(56) References Cited

U.S. PATENT DOCUMENTS

| 4,564,628 A | 1/1986 | Horn |
| 4,943,428 A | 7/1990 | Lucot et al. |
| 5,189,037 A | 2/1993 | Seymour |
| 5,739,151 A | 4/1998 | McCullough et al. |

FOREIGN PATENT DOCUMENTS

| WO | WO 1999/015160 | 4/1999 |
| WO | WO 2001/032263 | 5/2001 |
| WO | WO 2005/058296 | 6/2005 |
| WO | WO 2005/063238 | 7/2005 |

OTHER PUBLICATIONS

Andrews, P., *European Journal of Pharmacology*, 1996, vol. 307, No. 3, pp. 305-313.
Andrews, P.L., *British Journal of Pharmacology*, 2000, vol. 130, No. 6, pp. 1247-1254.
Brame, R.E., et al., Guamanian Suncus murinus responsiveness to emetic stimuli and the antiemetic effects of 8-OH-DPAT, *Pharmacology Biochemistry and Behavior*, 2011, vol. 99, No. 3, pp. 381-384.
Cao, B.J., "Different behavioural profiles of the R(+)- and S(−)-enantiomers of 8-hydroxy-2-(di-n-propylamino)tetralin in the murine elevated plus-maze," *Behavioural Pharmacology*, 1996, vol. 7, pp. 810-819.
Chen, Y., *Life Sciences*, 1997, vol. 60, Nos. 4-5, pp. 253-261.
Di Francesco, G.F., *European Journal of Pharmacology*, 1988, vol. 147, No. 2, pp. 287-290.
Javid, F.A., et al., *Pharmacology Biochemistry and Behavior*, 2002, vol. 73, No. 4, pp. 979-989.
Javid, F.A., et al., *Pharmacology Biochemistry and Behavior*, 2006, vol. 85, No. 4, pp. 820-826.
Lucot, J.B., et al., *Pharmacology Biochemistry and Behavior*, 1989, vol. 33, No. 3, pp. 627-631.
Lucot, J.B., *European Journal of Pharmacology*, 1990, vol. 180, Nos. 2-3, pp. 193-199.
Lucot, J.B., *Pharmacology Biochemistry and Behavior*, 1990, vol. 37, No. 2, pp. 283-287.
Lucot, J.B., et al., *Brain Research Bulletin*, 1991, vol. 26, No. 6, pp. 919-921.
Lucot, J.B., *European Journal of Pharmacology*, 1994, vol. 253, Nos. 1-2, pp. 53-60.
Okada, F., *Japanese Journal of Pharmacology*, 1994, vol. 64, No. 2, pp. 109-114.
Ramamoorthy, R., et al., *Behav. Pharmacol.*, 2008, vol. 19, No. 1, pp. 29-40.
Rock, E.M., et al., "Cannabidiol, a non-psychotropic component of cannabis, attenuates vomiting and nausea-like behaviour via indirect agonism of 5-HT(1A) somatodendritic autoreceptors in the dorsal raphe nucleus," *British Journal of Pharmacology*, 2012, vol. 165, No. 8, pp. 2620-2634.
Rock, E.M., et al., "Interaction between non-psychotropic cannabinoids in marihuana: effect of cannabigerol (CBG) on the anti-nausea or anti-emetic effects of cannabidiol (CBD) in rats and shrews," *Psychopharmacology*, 2011, vol. 215, No. 3, pp. 505-512.
Rudd, J.A., *European Journal of Pharmacology*, 1999, vol. 374, No. 1, pp. 77-84.
Wolff, M.C., et al., *Pharmacology Biochemistry and Behavior*, 1994, vol. 49, No. 2, pp. 385-391.
Yoshida, N., et al., "A dopamine 03 receptor agonist, 7-0H-DPAT, causes vomiting in the dog," *Life Sciences*, 1995, vol. 57, No. 21, pp. PL347-PL350.
Translation of International Patent Application No. WO 2001/032263 of BASF Aktiengesellschaft, published May 10, 2001.
Translation of International Patent Application No. WO 2005/058296 of Schwarz Pharma AG, published Jun. 30, 2005.
Translation of International Patent Application No. WO 2005/063238 of Schwarz Pharma AG, published Jul. 14, 2005.

(Continued)

*Primary Examiner* — Kathrien A Cruz
(74) *Attorney, Agent, or Firm* — Loza & Loza, LLP; Michael Fedrick

(57) ABSTRACT

A method of treating or preventing emesis through the administration of an effective dosage of a 2-(amino)tetralin compound in which one of the S or R enantiomers of the 2-(amino) tetralin compound is present in the composition in excess of the other enantiomer, and compositions comprising such a 2-(amino)tetralin compound in which the ratio of the S and R enantiomers is at least 2:1.

18 Claims, 8 Drawing Sheets

(56) References Cited

OTHER PUBLICATIONS

International Search Report and Written Opinion for International Patent Application No. PCT/US2010/052961, dated Jul. 26, 2011.
International Preliminary Report on Patentability for International Patent Application No. PCT/US2010/052961, dated Apr. 17, 2012.
Supplementary European Search Report, European Patent Application No. 10824226.4, dated Mar. 24, 2014.

EMESIS TREATMENT

CROSS-REFERENCE TO RELATED APPLICATIONS

This application is a continuation of U.S. patent application Ser. No. 13/501,531, filed Apr. 12, 2012 and entitled EMESIS TREATMENT, which is the U.S. national stage of International Patent Application No. PCT/US2010/052961, filed on Oct. 15, 2010 and entitled EMESIS TREATMENT, which claims the benefit of priority from U.S. Patent Application No. 61/252,291, filed Oct. 16, 2009 and entitled TREATMENT AND PREVENTION OF EMESIS. The disclosures of the foregoing applications are incorporated herein by reference in their entirety.

BACKGROUND

Emesis (vomiting) is a common symptom of a variety of disorders, brought on by events including the administration of chemotherapeutic agents, motion, pregnancy (morning sickness), and infections. Anti-emetic therapy generally involves removing the offending stimulus or resolving the condition responsible for the emesis. There are only a limited number of medicinal remedies currently available for emesis, and these often have undesired side effects, such as sedation or anxiety.

The use of (±)-8-Hydroxy-2-(dipropylamino)tetralin [(±)-8-OH-DPAT] has been reported for the treatment of emesis (see, e.g., U.S. Pat. No. 4,943,428). The administration of racemic 8-OH-DPAT, however, has been found to cause anxiety in test subjects. Racemic 8-OH-DPAT therefore has not been developed for the treatment or prevention of emesis.

SUMMARY

There remains therefore a need for improved treatments for emesis, in particular treatments with improved side effect profiles. The present compositions for the treatment of emesis in mammals, which are non-sedating and have reduced anxiogenic effects, meet this need.

In one embodiment, the present method for the treatment of emesis in a mammal, such as a human, comprises the step of administering to the mammal a composition comprising S(−)-8-hydroxy-2-(dipropylamino)tetralin and R(+)-8-hydroxy-2-(dipropylamino)tetralin, wherein one of the S(−)-8-hydroxy-2-(dipropylamino)tetralin or the R(+)-8-hydroxy-2-(dipropylamino)tetralin is present in the composition in a greater amount. The type of emesis treated can be, for example, delayed emesis or anticipatory emesis. Such emesis can be associated with pregnancy, migraine headache, motion, exposure to chemical agents, exposure to radiation, viral infection, bacterial infection, or conditions or events associated with emesis.

In the present methods, the amount of S(−)-8-hydroxy-2-(dipropylamino)tetralin in the composition is preferably greater than the amount of R(+)-8-hydroxy-2-(dipropylamino)tetralin in the composition used for treatment. For example, the ratio of S(−)-8-Hydroxy-2-(dipropylamino)tetralin to R(+)-8-Hydroxy-2-(dipropylamino)tetralin present in the composition is at least 2:1, and more preferably is at least 8:1. The amount of S(−)-8-Hydroxy-2-(dipropylamino)tetralin administered can be at least 0.08 mg/kg, for example, such as between 0.08 mg/kg and 0.16 mg/kg, and the amount of R(+)-8-Hydroxy-2-(dipropylamino)tetralin administered is preferably less than 0.04 mg/kg.

In a particular embodiment, the present method for the treatment of emesis in a human or other mammal comprises administering to the mammal a composition comprising a mixture of S and R enantiomers of a 2-aminotetralin compound having the following formula:

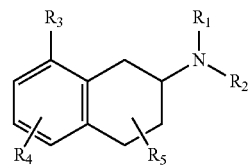

wherein:
$R_1$ and $R_2$ are each, independently, selected from the group consisting of hydrogen, $C_1$-$C_8$ alkyl, and $C_1$-$C_8$ alkenyl, or alternately, $R_1$ and $R_2$ can be taken together with the nitrogen to which they are attached to form a 5- to 8-membered nitrocyclic ring, wherein the alkyl, alkenyl, and nitrocyclic groups are unsubstituted, or can be substituted with one or more halide atoms.

$R_3$ is selected from the group consisting of OH, F, $NH_2$, $CH_3$, and SH;

$R_4$ and $R_5$ are each, independently, selected from the group consisting of hydrogen, halide, OH, $CF_3$, $C_1$-$C_8$ alkyl, and $C_1$-$C_8$ alkenyl, $COR_6$, and $OR_6$, wherein the alkyl and alkenyl groups are unsubstituted, or can be substituted with one or more halide atoms, and wherein $R_4$ and $R_4$ are each, independently substituted at the 1-, 3-, 4-, 5-, 6-, and 7-ring positions of the tetralin ring structure;

$R_6$ is selected from the group consisting of hydrogen, $C_1$-$C_5$ alkyl, $C_1$-$C_5$ alkenyl, and aminoalkyl, and wherein the composition comprises an excess amount of one of the S or R enantiomers of the compound of formula I.

In a particular embodiment, $R_1$ and $R_2$ are each independently $C_1$-$C_8$ alkyl, such as n-propyl; $R_3$ is OH; and $R_4$ and $R_5$ are each independently hydrogen, and the composition comprises an excess amount of the S enantiomer of the compound.

The present method for the treatment of emesis in a mammal can further comprise administering to a mammal a composition comprising a mixture of an S enantiomers of a 2-aminotetralin compound and an R enantiomer of a 2-aminotetralin compound, where the composition comprises an excess amount of at least one of the S enantiomer of the 2-aminotetralin compound or the R enantiomer of the 2-(amino)tetralin compound, and at least one of the S enantiomer of the 2-aminotetralin compound or the R enantiomer of the 2-(amino) tetralin compound has activity as a 5-$HT_{1A}$ agonist. The 2-aminotetralin compound in this embodiment can be (±)-8-hydroxy-2-(dipropylamino)tetralin, and the S enantiomer of the 8-hydroxy-2-(dipropylamino)tetralin can be present in the composition in an amount greater than the R enantiomer of the 8-hydroxy-2-(dipropylamino)tetralin.

The present invention further comprises a pharmaceutical composition comprising 8-hydroxy-2-(dipropylamino)tetralin in which the ratio of the S enantiomer of the 8-hydroxy-2-(dipropylamino)tetralin to the R enantiomer of the 8-hydroxy-2-(dipropylamino)tetralin can be between 2:1 and 10:1, and is more preferably between 4:1 and 8:1, and most preferably is about 8:1.

FIGURES

Figure 3:
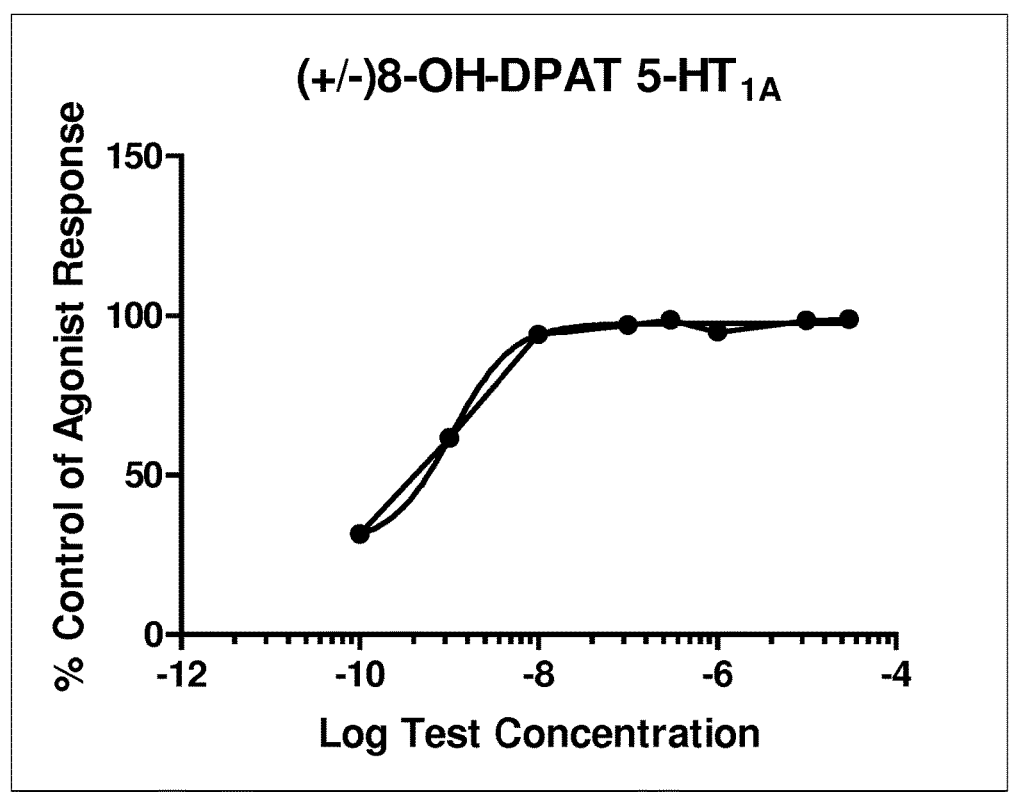

FIG. 3 is a graph representing the functional activity of racemic 8-OH-DPAT at the $5\text{-}HT_{1A}$ human receptor ligand, showing the agonist response of racemic 8-OH-DPAT (as a percent of the response of a known agonist of $5\text{-}HT_{1A}$) versus the log of the molar concentration of racemic 8-OH-DPAT.

Figure 4:
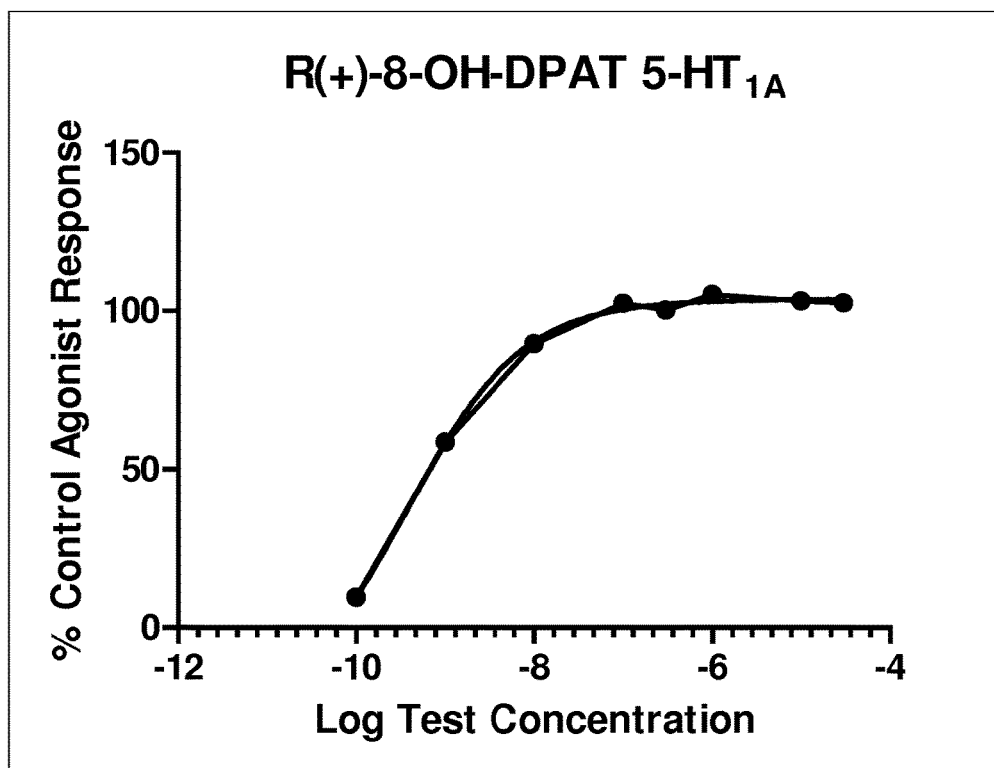

FIG. 4 is a graph representing the functional activity of R(+)-8-OH-DPAT at the $5\text{-}HT_{1A}$ human receptor ligand, showing the agonist response of R(+)-8-OH-DPAT (as a percent of the response of a known agonist of $5\text{-}HT_{1A}$) versus the log of the molar concentration of R(+)-8-OH-DPAT.

Figure 5:
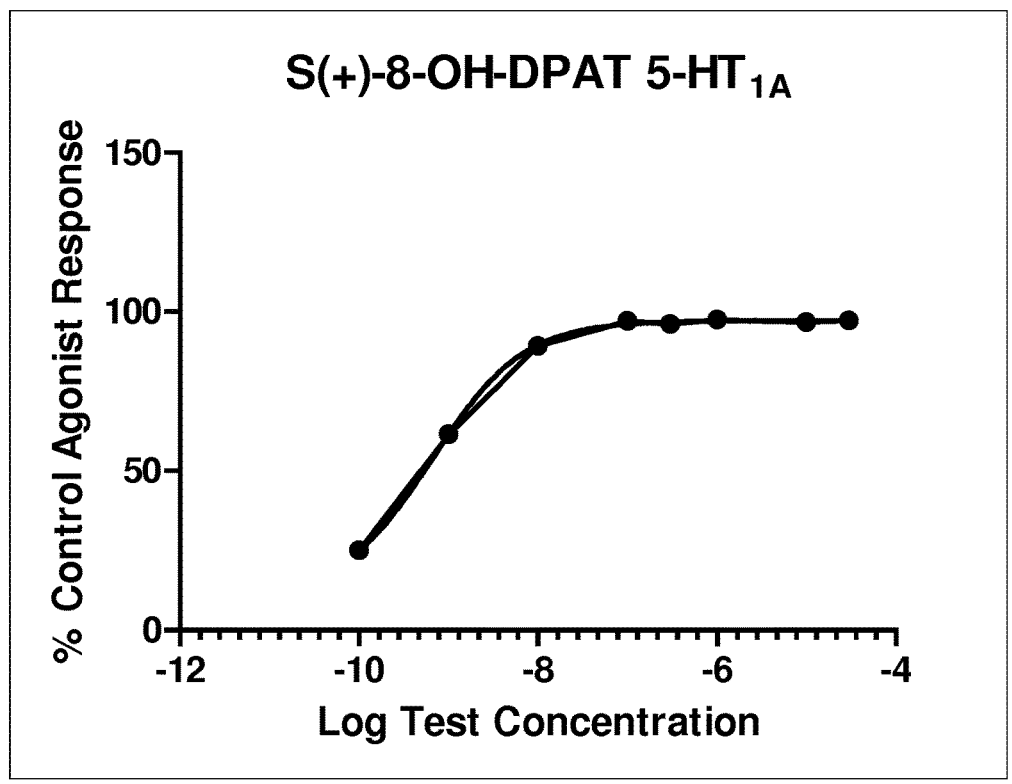

FIG. 5 is a graph representing the binding affinity of S(−)-8-OH-DPAT at the $5\text{-}HT_{1A}$ human receptor ligand, showing the agonist response of S(−)-8-OH-DPAT (as a percent of the response of a known agonist of $5\text{-}HT_{1A}$) versus the log of the molar concentration of S(−)-8-OH-DPAT.

Figure 6:
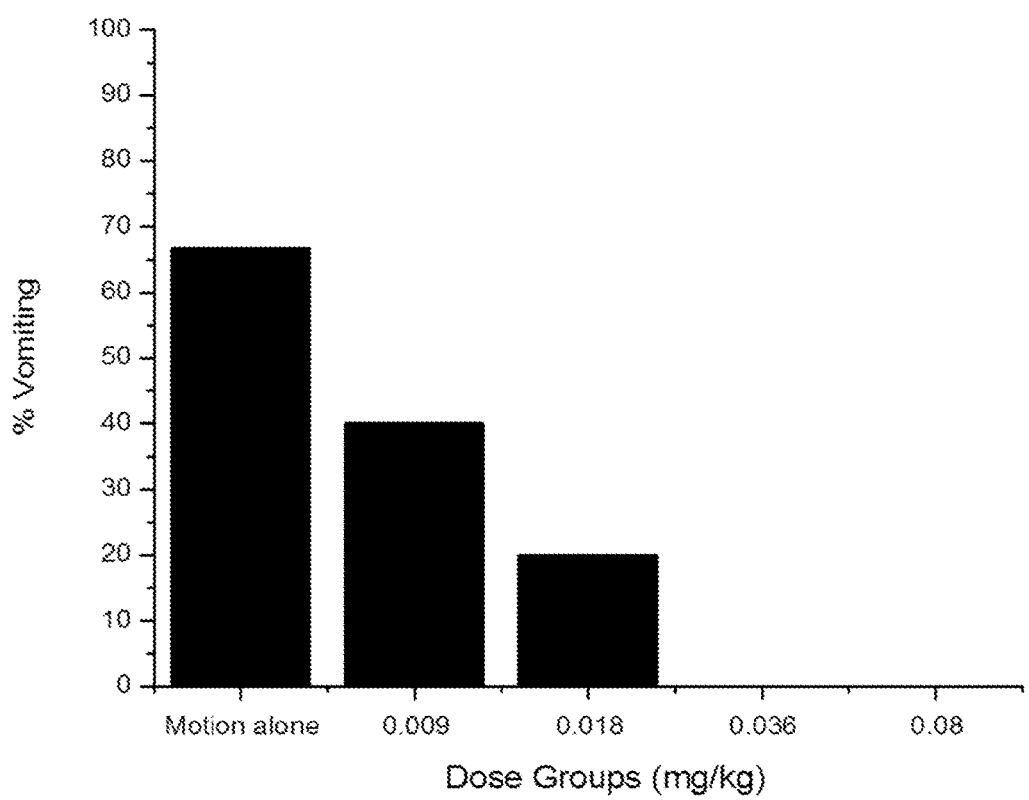

FIG. 6 is a bar graph showing the amount of protection from vomiting provided by the present 8-OH-DPAT compositions at varying dosages in male shrews in a model of emesis induced by motion.

Figure 7:
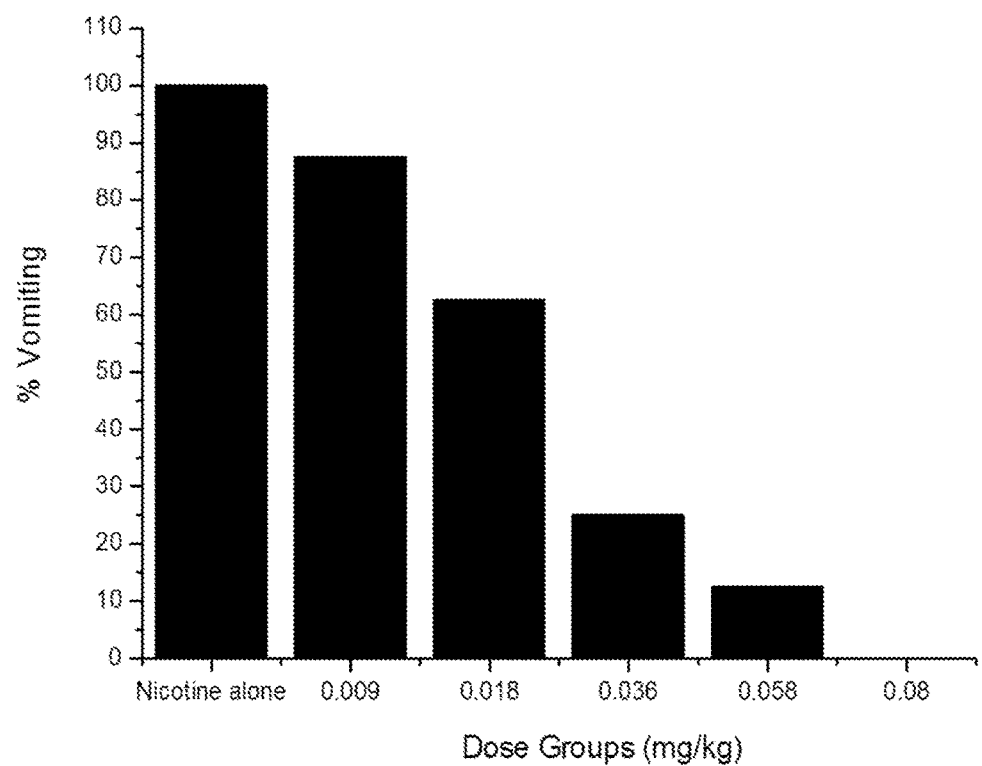

FIG. 7 is a bar graph showing the amount of protection from vomiting provided by the present 8-OH-DPAT compositions at varying dosages in female shrews in a model of emesis induced by nicotine tartarate.

Figure 8:
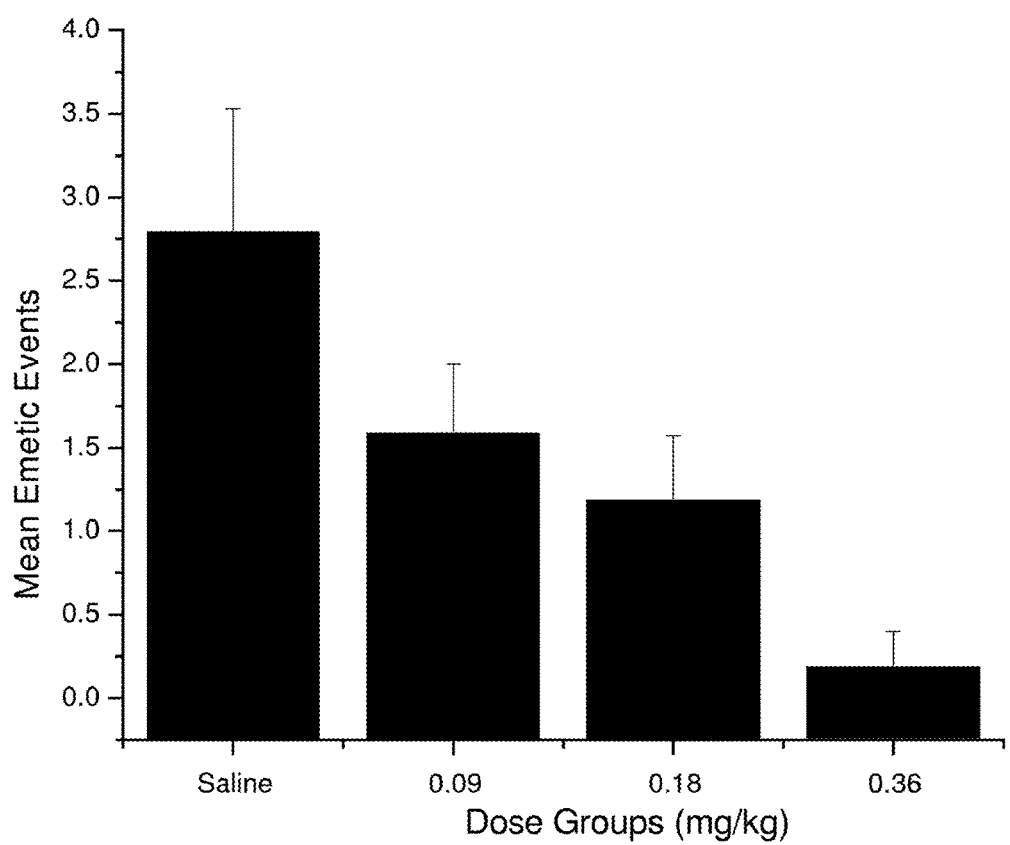

FIG. 8 is a bar graph showing the amount of protection from vomiting provided by the present 8-OH-DPAT compositions at varying dosages in female shrews in a model of emesis induced by cisplatin.

DESCRIPTION

The present methods for treating emesis and/or nausea in a mammal comprise administering to the mammal a composition comprising a mixture of an effective dosage of a 2-aminotetralin compound, where one of the S or R enantiomers of the 2-aminotetralin compound is present in the composition in excess of the other enantiomer. The composition is effective in treating emesis with a reduced side effect profile compared to current therapeutic agents.

Definitions

As used herein, the following terms and variations thereof have the meanings given below, unless a different meaning is clearly intended by the context in which such term is used.

"About" when used in reference to a numerical value means plus or minus ten percent of the indicated amount. For example and not by way of limitation, "about 10" means between 9 and 11, and "about 10%" means between 9% and 11%.

"2-aminotetralin" refers to a 1,2,3,4-tetrahydronaphthalene, substituted in the 2-position with an amino group (—$NR_1R_2$), as shown below, with the positions in the tetralin ring system also designated below.

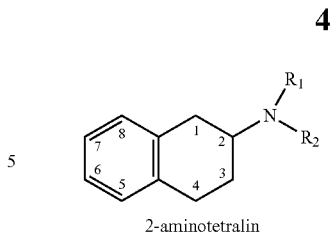

2-aminotetralin

"8-(OH)-DPAT" is (±)-8-Hydroxy-2-(dipropylamino)tetralin.

"Anticipatory emesis" refers to a conditioned vomiting response, i.e. emesis that occurs in a subject before the subject is exposed to a substance, agent, or event (such as exposure to a chemotherapeutic agent) which has previously caused the subject to experience emesis.

"Anxiety" refers to a sense of apprehension and fear often marked by physical symptoms (such as sweating, tension, and increased heart rate). Anxiety can be measured in clinical and preclinical models known to those of skill in the art.

"Anxiogenic" describes a substance, agent, event, or condition that causes anxiety.

"Delayed emesis" means emesis that occurs in a subject more than 24 hours after the subject is exposed to a substance, agent, or event which results in the subject experiencing emesis, or that occurs more than 24 hours after the subject contracts a condition which results in the subject experiencing emesis.

"Emesis" refers to vomiting, i.e., the reflex act of ejecting the contents of the stomach through the mouth.

"Enantiomer" means a compound that is one of two stereoisomers that are nonsuperimposable complete mirror images of each other.

"Enantiomeric excess" describes a composition in which one enantiomer is present in an amount which exceeds the amount of the other entantiomer in the composition, and is defined as the absolute difference between the mole fraction of each enantiomer. This can be expressed formulaically as follows:

$$ee=|F_+-F_-|$$

where $$F_++F_-=1.$$

"Nausea" refers to a sensation of unease and discomfort in the stomach accompanied by an urge to vomit. Nausea can be measured in ways known to the art, such as through the use of a visual analog scale (VAS).

"Percent enantiomeric excess" means the enantiomeric excess expressed as a percentage. For example, a sample with 70% of S isomer and 30% of R will have an enantiomeric excess of 40%. This can also be thought of as a mixture of 40% pure S with 60% of a racemic mixture (which contributes 30% R and 30% S to the overall composition).

"Treatment," in the context of treating emesis by administering one of the compositions disclosed herein, includes both prophylactic treatment and the treatment of emesis after a subject experiences emesis. Prophylactic treatment includes administration of a composition before a subject experiences emesis, such as when the subject experiences nausea, as well as administration of the composition before the subject is exposed to a substance, agent, or event, or before the subject contracts a condition, which results in or is likely to result in the subject experiencing emesis.

As used herein, the term "comprise" and variations of the term, such as "comprising" and "comprises," are not intended to exclude other additives, components, integers or steps. The terms "a," "an," and "the" and similar referents used herein are to be construed to cover both the singular and the plural unless their usage in context indicates otherwise.

2-Aminotetralin Compounds

The present compositions comprise improved mixtures of the S and R enantiomers of a 2-aminotetralin compound of formula I:

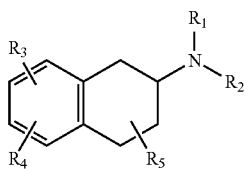

wherein:
- $R_1$ and $R_2$ are each, independently, selected from the group consisting of hydrogen, $C_1$-$C_8$ alkyl, and $C_1$-$C_8$ alkenyl, or alternately, $R_1$ and $R_2$ can be taken together with the nitrogen to which they are attached to form a 5- to 8-membered nitrocyclic ring, wherein the alkyl, alkenyl, and nitrocyclic groups are unsubstituted, or can be substituted with one or more halide atoms;
- $R_3$ is selected from the group consisting of OH, F, $NH_2$, $CH_3$, and SH;
- $R_4$ and $R_5$ are each, independently, selected from the group consisting of hydrogen, halide, OH, $CF_3$, $C_1$-$C_8$ alkyl, and $C_1$-$C_8$ alkenyl, $COR_6$, and $OR_6$, wherein the alkyl and alkenyl groups are unsubstituted, or can be substituted with one or more halide atoms, and wherein $R_4$ and $R_4$ are each, independently substituted at the 1-, 3-, 4-, 5-, 6-, and 7-ring positions of the tetralin ring structure; and
- $R_6$ is selected from the group consisting of hydrogen, $C_1$-$C_5$ alkyl, $C_1$-$C_5$ alkenyl, and aminoalkyl.

In a preferred embodiment, $R_1$ and $R_2$ are each independently $C_1$-$C_8$ alkyl; $R_3$ is OH; and $R_4$ and $R_5$ are each independently hydrogen. $R_1$ and $R_2$ can for example, each independently be n-propyl.

In a further preferred embodiment, the 2-aminotetralin compound is a compound of formula II:

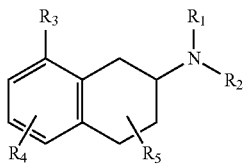

wherein the $R_1$, $R_2$, $R_3$, $R_4$ and $R_5$ groups are as described above for the 2-aminotetralin compound of formula I. In a particularly preferred embodiment, the 2-aminotetralin is 8-(OH)-DPAT.

2-Aminotetralin Compositions

The present compositions comprise a compound according to formula I, such as 8-OH-DPAT, in which there exists an enantiomeric excess of one of the S or R enantiomers of the compound. Preferably, the S enantiomer of a 2-aminotetralin compound (an "S-2-aminotetralin" compound) is in excess of the R enantiomer of the 2-aminotetralin compound (an "R-2-aminotetralin" compound), and such excess is a percent enantiomeric excess of at least about 50%, preferably at least 60%, and more preferably at least 80%. The ratio of S- to R- enantiomers used in the present compositions is preferably at least than 2:1, more preferably at least 4:1, and even more preferably at least 8:1, for example 10:1. Preferably, the ratio of the S-2-aminotetralin compound to the R-2-aminotetralin compound is an amount effective to prevent emesis without producing an anxiogenic effect.

Emesis can be treated by administering one or more of the present compositions, preferably including pharmaceutically acceptable excipients, to a mammal such as a human. The present compounds are beneficial in the treatment of acute, delayed or anticipatory emesis, including emesis induced by chemotherapy, radiation, toxins, viral or bacterial infections, pregnancy, vestibular disorders (e.g. motion sickness, vertigo, dizziness and Meniere's disease), surgery, migraine, and variations in intracranial pressure. The use of the present compositions is also of benefit in the therapy of emesis induced by radiation, for example during the treatment of cancer, and in the treatment of post-operative nausea and vomiting. The use of the present compositions is also beneficial in the therapy of emesis induced by antineoplastic (cytotoxic) agents including those routinely used in cancer chemotherapy, and emesis induced by other pharmacological agents. Further, the present compositions can also be used in the therapy of acute, delayed or anticipatory emesis from an unknown cause. In addition to treating emesis, the present compositions can be used to treat nausea.

8-OH-DPAT Compositions

In one embodiment, the present compositions comprise non-racemic mixtures of 8-OH-DPAT enantiomers. We have found that the R- enantiomer of 8-OH-DPAT, administered alone, is 100% effective in preventing chemically-induced emesis, but has a moderate to strong anxiety-inducing effect when administered to test subjects. We have further discovered that the S- enantiomer of 8-OH-DPAT, although not fully effective in preventing chemically induced emesis when administered as a sole agent, induces no anxiety or only slight anxiety in test subjects. By altering the ratios of the R- and S- enantiomers in a mixture of 8-OH-DPAT enantiomers, therefore, the present inventors have produced a composition with improved properties. A specific combination of the S(−) and R(+) isomers of 8-OH-DPAT can be used in the treatment of emesis in a mammal, preferably a human, without anxiogenic effects.

Figure 1:
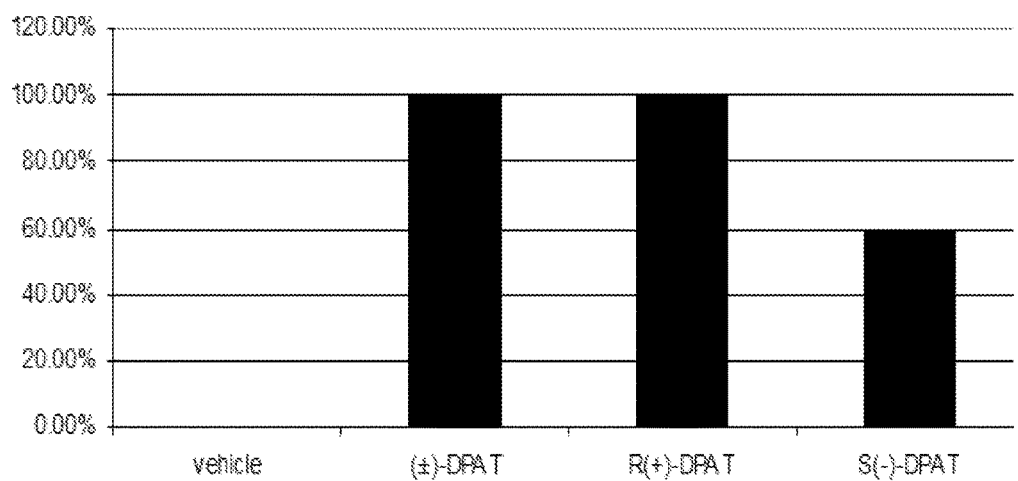
FIG. 1 is a bar graph showing the amount of protection from vomiting provided by 8-OH-DPAT compositions in female cats in a model of emesis induced by xylazine.

This conclusion is illustrated in FIG. 1, which shows data gathered from a test of female domestic short-haired felines which were subcutaneously (SC) administered either:
(i) 0.9% sodium chloride vehicle (n=6);
(ii) 0.16 mg/kg of (±)-8-Hydroxy-2-(dipropylamino)tetralin hydrobromide (n=6);
(iii) 0.08 mg/kg R(+)-8-Hydroxy-2-(dipropylamino)tetralin hydrobromide (n=6); or
(iv) 0.08 mg/kg S(−)-8-Hydroxy-2-(dipropylamino)tetralin hydrobromide (n=5).

Fifteen minutes later, 0.66 mg/kg xylazine was administered subcutaneously, and the test subjects where then observed for 30 minutes. As shown in the first bar of FIG. 1, when the 0.9% sodium chloride vehicle was administered to the cats, all the cats vomited, exhibiting 0% protection against xylazine-induced emesis, and none of the cats showed any anxiety 15 minutes after treatment with the vehicle. When the racemic mixture of (±)-8-Hydroxy-2-(dipropylamino)tetralin hydrobromide was administered to the cats, none of the cats vomited, exhibiting 100% protection against xylazine-induced emesis, but the cats showed a moderate level of anxiety 15 minutes after treatment (second bar of FIG. 1). As shown in the third bar of FIG. 1, when R(+)-8-Hydroxy-2-(dipropylamino)tetralin hydrobromide was administered to the cats as a sole agent, none of the cats vomited, but the cats showed an extreme level of anxiety 15 minutes after treatment. By contrast, when S(−)-8-Hydroxy-2-(dipropylamino)tetralin hydrobromide was administered to the cats, 40% of cats vomited, exhibiting 60% protection against xylazine-induced emesis, and the cats did not show any anxiety 15 minutes after treatment (fourth bar of FIG. 1). Accordingly, a specific combination of the S(−) and R(+) isomers of a 2-aminotetralin compound has been found to be useful for the treatment of emesis in a mammal without an anxiogenic effect.

Further testing revealed that an excess of the S-enantiomer of 8-OH-DPAT can produce a composition which blocks emesis without producing anxiety. The ratio of S- to R- enantiomers used in the present 8-OH-DPAT compositions is preferably at least greater than 2:1, and more preferably at least 4:1. A particularly preferred ratio of S- to R- 8-(OH)-DPAT is an eight to one (8:1) excess of S(−) 8-OH-DPAT, which has been found to provide complete protection against emesis and no anxiety in test subjects. When administered to test subjects, the amount of S(−)-8-(OH)-DPAT administered is preferably at least 0.08 mg/kg, and more preferably between 0.08 mg/kg and 0.16 mg/kg. The amount of R(+)-8-(OH)-DPAT administered in such compositions is also preferably less than 0.04 mg/kg.

When mixtures of non-racemic 8-(OH)-DPAT of the present invention are administered to a subject, such as compositions comprising ratios of S-8-(OH)-DPAT to R-8-(OH)-DPAT of 2:1, 4:1, 8:1 or more, such compositions are preferably administered in amounts of at least 0.01 mg/kg, more preferably of at least 0.02 mg/kg, 0.03 mg/kg, or 0.05 mg/kg, and even more preferably of at least 0.08 mg/kg. The foregoing dosing is appropriate, in particular, for motion-induced emesis and emesis resulting from some chemical stimuli. For other chemicals or some environmental triggers for emesis, such as radiation, more potent doses of the present compositions may be required, for example at least 0.2 mg/kg, 0.3 mg/kg, 0.5 mg/kg, or 0.8 mg/kg or greater. One of skill in the art can determine an appropriate dose for a particular subject.

The present 8-OH-DPAT compositions therefore comprise amounts of the R-enantiomer of 8-OH-DPAT which are sufficient to substantially or completely block emesis in mammals, but which do not produce the anxiety associated with racemic mixtures of 8-OH-DPAT. Without being bound to a particular theory, the inventors believe that the S-enantiomer of 8-OH-DPAT blocks the anxiogenic effects of racemic 8-OH-DPAT, in particular of the R-enantiomer of 8-OH-DPAT. Accordingly, by varying the ratio of the S- to R- enantiomers of 8-(OH)-DPAT, preferably so as to produce an excess of the S- enantiomer, both an anti-emetic and an anti-anxiogenic effect can be achieved.

Previous findings suggest that R(+)-8-OH-DPAT is a full agonist of the 5-HT$_{1A}$ receptor and that S(−)-8-OH-DPAT is a partial agonist at the 5-HT$_{1A}$ receptor. (See, e.g., Cornfield L. et al., *Mol. Pharmacol.*, 1991, 39, 780; Hadrava V. et al., *J Psychiatry Neurosci.*, 1996, 21(2), 101-8; and Dabrowska J. et al., *Biochem. Pharmacol.*, 2006, 72, 498-511). Contrary to these findings, in which both R(+)-8-OH-DPAT and S(−)-8-OH-DPAT underwent cellular functional assays using the rat ligand of the 5-HT$_{1A}$ receptor, both R(+)-8-OH-DPAT and S(−)-8-OH-DPAT are full agonists of the 5-HT$_{1A}$ human receptor ligand.

The invention can be appreciated in certain aspects with reference to the following examples, offered by way of illustration, not by way of limitation. Materials, reagents and the like to which reference is made in the following examples are obtainable from commercial sources, unless otherwise noted.

EXAMPLES

Example 1

Blocking Xylazine-induced Emesis

I. Animal Preparation

A. Quarantine: Upon arrival the animals were examined to ensure that they were healthy and were quarantined for at least seven days before placement on study. At the end of the quarantine period, the general health of the animals was examined. Any unhealthy animals were not used in the study.

B. Food and Housing: The animals were housed in individual hanging stainless steel cages. They received Laboratory Feline Diet 5003 (available from Purina Mills, LLC, Gray Summit, Mo.). The animals were provided tap water ad libitum.

II. Experimental Procedure

A. Fasting: Animals had free access to food and water until the time of testing.

B. Motion Screening and Testing:

1. A motion stimulus was provided by a "felis wheel", a motor-driven device that resembles an amusement park Ferris wheel. The cats rode in clear plastic boxes suspended from two 0.445 m arms that rotated about the central horizontal axis at 0.28 Hz (17 rpm). Motion tests lasted for 30 minutes of rotation followed by one minute of observation at rest.

2. Animals were screened for motion sickness susceptibility by being tested through the felis wheel three times. Those cats that became adequately motion sick (i.e. vomited) on at least two out of three tests were considered adequately susceptible for motion testing.

3. For the evaluation of test compounds against motion sickness induced emesis, cats susceptible to motion sickness were initially injected subcutaneously with a freshly prepared solution of test compound in 0.9% sodium chloride or vehicle (injection volume of 0.1 ml/kg) 15 minutes prior to felis wheel exposure.

4. Vehicle or test compound evaluation in motion sickness induced emesis: After the 15 minute subcutaneous pretreatment with either vehicle or test compound animals rode in clear plastic boxes suspended from two 0.445 m arms that rotated about the central horizontal axis at 0.28 Hz (17 rpm). Observation took place during the motion tests that last for 30 minutes of rotation followed by an additional one minute of observation at rest. Behavioral scoring was completed using the vomit scale.

III. Xylazine-induced Emesis

Cats not susceptible to motion sickness were assigned to the xylazine testing group. Xylazine stimulates receptors on a pathway different from that used by motion sickness and thus served as a test of the generality of anti-emetic effects observed with motion testing.

Prior to the evaluation of anti-emetic compounds, the production of an emetic response by xylazine in felines was confirmed in the laboratory. Cats were injected subcutaneously with either a freshly prepared solution of 0.66 mg/kg of xylazine in 0.9% sodium chloride or 0.9% sodium chloride vehicle, both adjusted to an injection volume of 0.1 ml/kg.

data from the nonparametric rating scale was analyzed using Friedman's analysis of variance model (ANOVA).

VI. Results

A. Summary of Xylazine-Induced Emesis Results in Felines.

As shown below in Table I, varying doses of R-(+)-DPAT and S-(−)-DPAT were administered to cats not susceptible to motion sickness.

TABLE I

| Compound / Composition | Compound Dose (mg/kg) | Mean Latency* | % Protection (vomiting) | Mean Defensive Score | Defensive Behavior Scale | n = |
|---|---|---|---|---|---|---|
| R/S-(+/−)-DPAT | 0.16 | 0.0 | 100.00 | 2.0 | Moderate | 5 |
| R-(+)-DPAT | 0.02 | 0.00 | 100.00 | 2.0 | Moderate | 5 |
| R-(+)-DPAT | 0.04 | 0.00 | 100.00 | 3.0 | Strong | 3 |
| R-(+)-DPAT | 0.08 | 0.00 | 100.00 | 3.0 | Strong | 6 |
| S-(−)-DPAT | 0.08 | 1.58 | 75.00 | 0.0 | None | 4 |
| S-(−)-DPAT | 0.16 | 0.82 | 85.71 | 0.0 | None | 7 |
| S-(−)-DPAT | 0.32 | 1.00 | 80.00 | 1.0 | Slight | 5 |
| SALINE | 0.00 | 5.06 | 0.00 | 0.0 | None | 7 |
| R-(+)-DPAT + S-(−)-DPAT | 0.02 (R-(+)-DPAT)/ 0.08 (S-(−)-DPAT) | 0.74 | 83.33 | 1.0 | Slight | 6 |
| R-(+)-DPAT + S-(−)-DPAT | 0.04 (R-(+)-DPAT)/ 0.08 (S-(−)-DPAT) | 5.00 | 75.00 | 2.0 | Moderate | 4 |
| R-(+)-DPAT + S-(−)-DPAT | 0.02 (R-(+)-DPAT)/ 0.16 (S-(−)-DPAT) | 0.00 | 100.00 | 0.6 | None | 5 |
| R-(+)-DPAT + S-(−)-DPAT | 0.04 (R-(+)-DPAT)/ 0.16 (S-(−)-DPAT) | 2.23 | 40.00 | 0.6 | None | 5 |

*Latency is the mean latency to retch/vomit, in minutes.

One week following the confirmation of an emetic response by the cats, subject cats were given either vehicle or test compound/composition in 0.9% sodium chloride or vehicle (injection volume of 0.1 ml/kg) subcutaneously, 20 minutes before administration of xylazine. Cats were observed for 30 minutes following xylazine treatment or for 15 minutes after the last emetic episode, whichever occurred later Animals were scored using the vomit scale developed by Suri et al., 1979. Additional experiments were separated by at least a 1 week washout period.

IV. Data Collection

A. Vomit Scale Scoring:
1. Sal I (licking—parasympathetic): 1 pt
2. Sal II (drool, thin/frothy—early sympathetic): 2 pts
3. Sal III (stringy saliva, dangles—sympathetic): 4 pts
4. Defection: 8 pts
5. Urination: 8 pts
6. Wretch/vomiting: 16 pts B. Defensive Behavior Scale:
1. No defensiveness: normal behavior;
2. Slight defensiveness: retreating to the rear of the cage when approached and/or growling when being carried;
3. Moderate defensiveness: exhibiting flattened ears and trying to claw and bite when being carried;
4. Strong defensiveness: vigorous clawing and biting to prevent being handled.

V. Statistical Methods

Dose response curves were analyzed by Cochran's Q-test to establish significant effects. Paired comparisons were made using McNemar's test. Tests for line parallelism, relative potency and ED50 were based on least squares regression in a program for pharmacological statistics. The Example 2

Blocking Cisplatin-induced Emesis

Further experiments were performed as outlined in Example 1 above, except that the emesis-inducing agent used in the tests was cisplatin in place of xylazine. The cats were injected subcutaneously with either cis-platin or a sodium chloride vehicle. As shown below in Table II, an 8:1 ratio of S-(−)-DPAT to R-(+)-DPAT was administered to cats.

The cats were observed and scored using the vomit scale and defensive score described above.

TABLE II

| Compound | Mean Score | Mean Latency (min) | % Protection (vomiting) | Mean Emetic Events | Mean Defensive Score |
|---|---|---|---|---|---|
| 0.02 mg/kg R(+)-DPAT/0.16 mg/kg S(−)-DPAT | 19 | 251.80 | 40.00 | 2 | none |
| 0.9% sodium chloride | 27 | 62.20 | 0.00 | 8 | none |

Example 3

5-HT$_{1A}$ In-Vitro Analysis

A. Binding Affinity.

Figure 2:
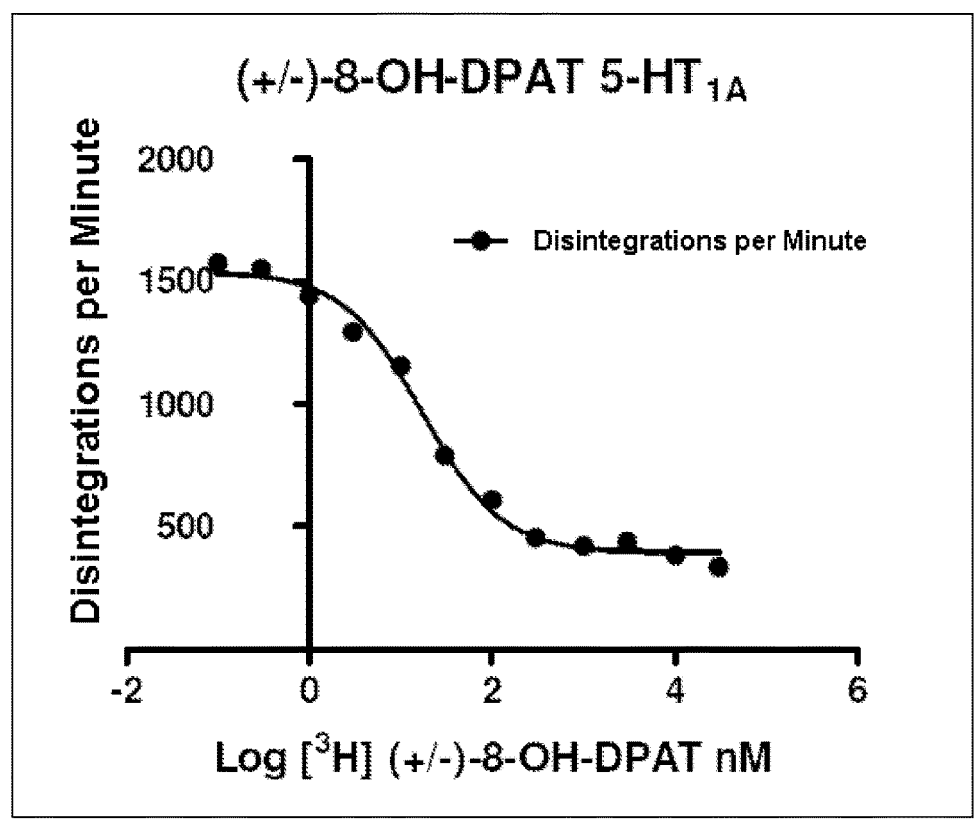
FIG. 2 is a graph representing the binding affinity of racemic 8-OH-DPAT at the $5HT_{1A}$ human receptor ligand.

The percent inhibition of agonist response was recorded for several molar log concentrations of the compositions listed below in Table III. As represented graphically in FIG. 2, racemic (+/−)-8-OH-DPAT has a high binding affinity for the 5-HT$_{1A}$ receptor (Ki=0.62 nM) (Table III, FIG. 2). Likewise, R(+)-8-OH-DPAT and S(−)-8-OH-DPAT also have high binding affinities for the 5-HT$_{1A}$ receptor (Ki=0.62 nM and 0.5 nM, respectively) (Table III).

B. Cellular Functionality.

The percent of control agonist response was recorded for several log concentrations of compounds/compositions. As shown in FIG. 3 and Table III, racemic (+/−)-8-OH-DPAT is a potent agonist of the 5-HT$_{1A}$ receptor (EC$_{50}$=0.62 nM). Likewise, R(+)-8-OH-DPAT and S(−)-8-OH-DPAT are also potent agonists of the 5-HT$_{1A}$ receptor (EC$_{50}$=0.81 nM and 0.35 nM, respectively) (Table III, FIGS. 4 and 5). Contrary to previous findings (Cornfield L. et al., 1991, Hadrava V. et al., 1996, Dabrowska J. et al., 2006), both R(+)-8-OH-DPAT and S(−)-8-OH-DPAT are full agonists of the 5-HT$_{1A}$ receptor.

TABLE III

5-HT$_{1A}$ Receptor Binding Affinity (Human Ligand).

| | Binding (Ki, nM) | Cellular Function Agonist (EC$_{50}$, nM) | Cellular Function Antagonist (IC$_{50}$, nM) |
|---|---|---|---|
| (+/−)-8-OH-DPAT | 5.5 | 0.36 | Inactive |
| R(+)-8-OH-DPAT | 0.62 | 0.81, Full Agonist | Inactive |
| S(−)-8-OH-DPAT | 0.5 | 0.35 Full Agonist | Inactive |

Example 4

Blocking Motion-Induced and Chemically-Induced Emesis in Shrews

The ability of the present OH-DPAT compositions to block emesis was further tested in Asian house shrews (*Suncus murinus*) using both a motion-induced model of emesis and a chemically-induced model of emesis.

Motion-Induced Emesis

Animals for use in testing the present compounds in connection with motion-induced emesis were included only if they vomited on both of two consecutive tests prior being treated with the test compound or vehicle. Male shrews were found to be more susceptible to emesis and were used for motion studies. In addition, test subjects received one test with saline alone to test for conditioned vomiting. A repeated measures design was employed. All tests were separated by one week to prevent habituation.

Motion sickness was induced by placing animals in individual holders (10×15×12 cm) mounted on a linear reciprocating shaker. Test subjects had five minutes of acclimation followed by ten minutes of motion at 1 Hz and 30 mm excursion. The latency for each emesis event and the number of events was recorded for each shrew. The composition used in Example 2, comprising an 8:1 ratio of S-(−)-DPAT to R-(+)-DPAT, was administered subcutaneously 15 minutes before motion was initiated in doses of 0.009 mg/kg, 0.018 mg/kg, 0.036 mg/kg, and 0.08 mg/kg.

Each test was videotaped for scoring and then archived. The duration of the retch/vomit sequence for each test animal was roughly two seconds. Incidents of violent dorsoflexion with flexion/extension of the hindquarters were counted as indications of emesis with or without the presence of vomitus. Tests with the stimulus alone were conducted at the end of the dose-response curve to verify that habituation had not occurred.

The results of the foregoing tests are shown in FIG. 6. As can be seen in that figure, approximately 65% of the animals not treated with the test compound experienced emesis, while the treated animals experienced reduced or no emesis in a dose-dependent manner. Animals treated with 0.036 and 0.08 mg/kg of the test compound experienced no emesis.

Drug Induced Emesis

Animals evaluated in the motion-induced emesis test described above which did not evidence emesis as a result of motion, primarily female shrews, were assigned to be tested in a model of drug induced emesis. Shrews in this group received 10 mg/kg of nicotine tartarate subcutaneously and were then monitored for 30 minutes. The number of episodes of emesis and the latency for each event were recorded. The test compound used in Example 2, comprising an 8:1 ratio of S-(−)-DPAT to R-(+)-DPAT, was administered subcutaneously 15 minutes before the nicotine compound was administered. The doses of the test compound administered were 0.009 mg/kg, 0.018 mg/kg, 0.036 mg/kg, 0.058 mg/kg, and 0.08 mg/kg.

The only prodromal observation (indicating the onset of emesis) was the observation of reduced motor activity before emesis. Animals were observed for retching and emetic responses for 90 minutes post-dosing. Tests were conducted at the end of the dose-response curve involving injecting saline alone in order to look for conditioned vomiting.

The results of the foregoing tests are shown in FIG. 7. As can be seen in that figure, all of the animals not treated with the test compound, i.e. treated only with nicotine tartarate, experienced emesis, while the treated animals experienced reduced or no emesis in a dose-dependent manner. Animals treated with 0.08 mg/kg of the test compound experienced no emesis.

A group of shrews were also tested for emesis in response to the administration of 20 mg/kg of cisplatin intraperitoneally using the protocol described above, except that the test compound was administered 30 minutes after cisplatin administration. The results are shown in FIG. 8, which shows a reduction in emesis in the treated animals in a dose-dependent manner, with animals receiving at least 0.36 mg/kg of the test compound exhibiting a statistically significant reduction in symptoms of emesis.

Although the present invention has been described in considerable detail with reference to certain preferred embodiments, other embodiments are possible. The steps disclosed for the present methods, for example, are not intended to be limiting nor are they intended to indicate that each step is necessarily essential to the method, but instead are exemplary steps only. Therefore, the scope of the appended claims should not be limited to the description of preferred embodiments contained in this disclosure. All references cited herein are incorporated by reference in their entirety.

What is claimed is:

1. A method for the treatment of emesis in a mammal, comprising the step of administering to the mammal a composition comprising S(−)-8-hydroxy-2-(dipropylamino)tetralin and R(+)-8-hydroxy-2-(dipropylamino)tetralin, wherein the ratio of the S enantiomer of the 8-hydroxy-2-(dipropylamino)tetralin to the R enantiomer of the 8-hydroxy-2-(dipropylamino)tetralin is about 8:1.

2. The method of claim 1, wherein the mammal is a human.

3. The method of claim 1, wherein the emesis is delayed emesis.

4. The method of claim 1, wherein the emesis is anticipatory emesis.

5. The method of claim 1, wherein the amount of S(−)-8-Hydroxy-2-(dipropylamino)tetralin administered is at least 0.08 mg/kg.

6. The method of claim 1, wherein the amount of S(−)-8-Hydroxy-2-(dipropylamino)tetralin administered is between 0.08 mg/kg and 0.16 mg/kg.

7. The method of claim 1, wherein the amount of R(+)-8-Hydroxy-2-(dipropylamino)tetralin administered is less than 0.04 mg/kg.

8. A method for the treatment of emesis in a mammal comprising, administering to the mammal a composition comprising a mixture of S and R enantiomers of a 2-aminotetralin compound of formula I:

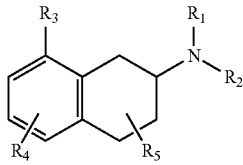

wherein:
- $R_1$ and $R_2$ are each, independently, selected from the group consisting of hydrogen, $C_1$-$C_8$ alkyl, and $C_1$-$C_8$ alkenyl, or alternately, $R_1$ and $R_2$ can be taken together with the nitrogen to which they are attached to form a 5- to 8-membered nitrocyclic ring, wherein the alkyl, alkenyl, and nitrocyclic groups are unsubstituted, or can be substituted with one or more halide atoms.
- $R_3$ is selected from the group consisting of OH, F, $NH_2$, $CH_3$, and SH;
- $R_4$ and $R_5$ are each, independently, selected from the group consisting of hydrogen, halide, OH, $CF_3$, $C_1$-$C_8$ alkyl, and $C_1$-$C_8$ alkenyl, $COR_6$, and $OR_6$, wherein the alkyl and alkenyl groups are unsubstituted, or can be substituted with one or more halide atoms, and wherein $R_4$ and $R_4$ are each, independently substituted at the 1-, 3-, 4-, 5-, 6-, and 7-ring positions of the tetralin ring structure;
- $R_6$ is selected from the group consisting of hydrogen, $C_1$-$C_5$ alkyl, $C_1$-$C_5$ alkenyl, and aminoalkyl, and wherein the ratio of the S enantiomer to the R enantiomer of the compound of formula I is about 8:1.

9. The method of claim 8, wherein, in the compound of formula I:
- $R_1$ and $R_2$ are each independently $C_1$-$C_8$ alkyl;
- $R_3$ is OH; and
- $R_4$ and $R_5$ are each independently hydrogen.

10. The method of claim 8, wherein $R_1$ and $R_2$ are each independently n-propyl.

11. A method for the treatment of emesis in a mammal, comprising administering to the mammal a composition comprising a mixture of an S enantiomer of a 2-aminotetralin compound and an R enantiomer of a 2-aminotetralin compound, wherein
- the ratio of the S enantiomer of the 2-aminotetralin compound to the R enantiomer of the 2-aminotetralin compound is about 8:1; and
- at least one of the S enantiomer of the 2-aminotetralin compound or the R enantiomer of the 2-aminotetralin compound has activity as a 5-$HT_{1A}$ agonist.

12. The method of claim 11, wherein the 2-aminotetralin compound is (+)-8-hydroxy-2-(dipropylamino)tetralin.

13. The method of claim 1, wherein the ratio of the S enantiomer of the 8-hydroxy-2-(dipropylamino)tetralin to the R enantiomer of the 8-hydroxy-2-(dipropylamino)tetralin in the composition is less anxiogenic than a racemic mixture of S(−)-8-hydroxy-2-(dipropylamino)tetralin and R(+)-8-hydroxy-2-(dipropylamino)tetralin.

14. The method of claim 8, wherein the ratio of the S enantiomer to the R enantiomer of the compound of formula I is less anxiogenic than a racemic mixture of the S enantiomer and the R enantiomer of the compound of formula I.

15. The method of claim 11, wherein the ratio of the S enantiomer to the R enantiomer of the 2-aminotetralin compound is less anxiogenic than a racemic mixture of the S enantiomer and the R enantiomer of the 2-aminotetralin compound.

16. The method of claim 1, wherein emesis is treated in the subject without inducing anxiety or sedation in the subject.

17. The method of claim 8, wherein emesis is treated in the subject without inducing anxiety or sedation in the subject.

18. The method of claim 11, wherein emesis is treated in the subject without inducing anxiety or sedation in the subject.

* * * * *